US009321792B2

(12) United States Patent
Backer et al.

(10) Patent No.: US 9,321,792 B2
(45) Date of Patent: Apr. 26, 2016

(54) HYDROLYSABLE SILANES

(71) Applicant: Dow Corning Corporation, Midland, MI (US)

(72) Inventors: Michael Wolfgang Backer, Mainz (DE); Thomas Chaussee, Fontaines Saint Martin (FR); Olivier Debever, Lembeek (BE); Sebastien Grofils, Porcheresse (BE)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/362,632

(22) PCT Filed: Dec. 7, 2012

(86) PCT No.: PCT/EP2012/074730
§ 371 (c)(1),
(2) Date: Jun. 4, 2014

(87) PCT Pub. No.: WO2013/083743
PCT Pub. Date: Jun. 13, 2013

(65) Prior Publication Data
US 2014/0364627 A1 Dec. 11, 2014

(30) Foreign Application Priority Data
Dec. 8, 2011 (GB) .................... 1121133.1

(51) Int. Cl.
*C07F 7/10* (2006.01)
*C07F 7/18* (2006.01)
*C08K 5/544* (2006.01)
*C07F 7/08* (2006.01)

(52) U.S. Cl.
CPC ............ *C07F 7/1804* (2013.01); *C07F 7/0818* (2013.01); *C07F 7/1836* (2013.01); *C07F 7/1872* (2013.01); *C08K 5/544* (2013.01)

(58) Field of Classification Search
None
See application file for complete search history.

(56) References Cited

U.S. PATENT DOCUMENTS

| | | |
|---|---|---|
| 2,853,488 A | 9/1958 | D'Amico et al. |
| 3,147,161 A | 9/1964 | Abere et al. |
| 3,169,122 A | 2/1965 | Hennes |
| 3,379,707 A | 4/1968 | Lund et al. |
| 3,408,198 A | 10/1968 | Reynolds et al. |
| 3,779,703 A | 12/1973 | Tesoro |
| 3,810,843 A | 5/1974 | Slusarczuk et al. |
| 3,855,241 A | 12/1974 | Wilkus et al. |
| 3,928,330 A | 12/1975 | Ramey et al. |
| 4,083,861 A | 4/1978 | Seiler et al. |
| 5,106,680 A | 4/1992 | King et al. |
| 5,369,143 A | 11/1994 | Kurimoto et al. |
| 5,821,277 A | 10/1998 | Hirayama et al. |
| 5,852,099 A | 12/1998 | Vanel |
| 6,494,946 B1 | 12/2002 | Belmont et al. |
| 6,794,428 B2 | 9/2004 | Burrington et al. |
| 6,806,339 B2 | 10/2004 | Cray et al. |
| 7,144,967 B2 | 12/2006 | Sakamoto et al. |
| 7,419,975 B2 | 9/2008 | Palermo et al. |
| 7,732,029 B1 | 6/2010 | Moorlag et al. |
| 7,833,404 B2 | 11/2010 | Matsuda et al. |
| 7,847,117 B2 | 12/2010 | Merget |
| 7,981,966 B2 | 7/2011 | Kobayashi et al. |
| 8,140,294 B2 | 3/2012 | Ramey et al. |
| 8,202,944 B2 | 6/2012 | Suzuki et al. |
| 8,318,858 B2 | 11/2012 | Oshima |
| 8,476,375 B2 | 7/2013 | Backer et al. |
| 8,524,836 B2 | 9/2013 | Kavanagh et al. |
| 8,569,417 B2 | 10/2013 | Backer et al. |
| 2005/0234042 A1 | 10/2005 | Palermo et al. |
| 2010/0056713 A1 | 3/2010 | Oshima |
| 2010/0137499 A1 | 6/2010 | Moorlag et al. |
| 2011/0049056 A1 | 3/2011 | Wyndham et al. |
| 2011/0146877 A1 | 6/2011 | Tanaka et al. |
| 2011/0172367 A1 | 7/2011 | Backer et al. |
| 2012/0059121 A1 | 3/2012 | Backer et al. |
| 2012/0065319 A1 | 3/2012 | Backer et al. |
| 2012/0270997 A1 | 10/2012 | Tanaka et al. |
| 2012/0277369 A1 | 11/2012 | Yoshida et al. |
| 2012/0330044 A1 | 12/2012 | Hou |
| 2013/0079464 A1 | 3/2013 | Nishioka et al. |

FOREIGN PATENT DOCUMENTS

| | | |
|---|---|---|
| DE | 206848 | 2/1984 |
| GB | 1123303 | 8/1968 |
| GB | 1214451 | 12/1970 |
| GB | 1473335 | 5/1977 |
| HU | 180661 | 4/1983 |
| JP | 5543143 | 3/1980 |
| JP | 10095933 | 4/1998 |
| JP | 2001240706 | 9/2001 |
| JP | 2004085689 | 3/2004 |
| JP | 2004085775 | 3/2004 |
| JP | 2004109586 | 4/2004 |
| JP | 2005249897 | 9/2005 |
| JP | 2008163283 | 7/2008 |
| WO | 9429324 | 12/1994 |
| WO | 0170866 | 9/2001 |
| WO | 2011083050 | 7/2011 |

OTHER PUBLICATIONS

Matsuo et al: "Introduction of amino groups into the interlayer space of graphite oxide using 3-aminopropylethoxysilanes", Carbon, Elsevier, Oxford, GB, vol. 45, No. 7, Jun. 1, 2007, pp. 1384-1390.

(Continued)

*Primary Examiner* — Michael Barker
(74) *Attorney, Agent, or Firm* — Matthew T. Fewkes

(57) ABSTRACT

This invention relates to hydrolysable silanes useful in the modification of elastomers, and as coupling agents for diene elastomer compositions containing a filler. In particular the invention relates to novel hydrolysable silanes containing an aziridine ring herein named (Az).

11 Claims, No Drawings

(56) References Cited

OTHER PUBLICATIONS

Organometallics, vol. 13(9), 1994, (Muehleisen, Mathias; Tacke, Reinhold), pp. 3740-3742.
Russian Journal of Applied Chemistry; vol. 82, Issue 5, pp. 928-930; Journal 2009; by V. M. Farzaliev, M. T. Abbasova, A. A. Ashurova, G. B. Babaeva, N. P. Ladokhina and Ya. M. Kerimova.
The Russian Chemical Bulletin, vol. 44(2), 1995, pp. 374-375.
The Vanderbilt Rubber Handbook (1978), pp. 344 through 346.
Journal of Membrane Science, vol. 129(2), 1997, Barbiou, Mihai et al, pp. 197-207.
European Journal of Organic Chemistry, vol. 13, 2006, (Bianco, Alberto et al.), pp. 2934-2941.
Gasparrini, F. et al., "Molecular recognition of p-tert-butylcalixarenes by surface-linked fullerenes C60 and C70", Tetrahedron, Elsevier Science Publishers, Amsterdam, NL, vol. 57, No. 32, Aug. 6, 2001, pp. 6997-7002.
Bianco et al., "Molecular recognition by a silica-bound fullerene derivative", J. Am. Chem. Soc. 1997, vol. 119, pp. 7550-7554.
Brunauer et al., Adsorption of Gases in Multimolecular Layers, Feb. 1938, pp. 309-319, vol. 60.
Chemische Berichte, vol. 120(4), 1987, Brueckmann, Ralf, et al., pp. 635-641.

HYDROLYSABLE SILANES

CROSS REFERENCE TO RELATED APPLICATIONS

This application is a U.S. national stage filing under 35 U.S.C. §371 of PCT Application No. PCT/EP12/74730 filed on 7 Dec. 2012, currently pending, which claims the benefit of GB Patent Application No. 1121133.1 filed 8 Dec. 2011 under 35 U.S.C. §119 (a)-(d) and 35 U.S.C. §365(a). PCT Application No. PCT/EP12/74730 and GB Patent Application No. 1121133.1 are hereby incorporated by reference.

This invention relates to hydrolysable silanes useful in the modification of elastomers, and as coupling agents for diene elastomer compositions containing a filler. In particular the invention relates to novel hydrolysable silanes containing an aziridine ring herein named (Az).

WO-A-2010/139473 describes various hydrolysable silanes as coupling agents between an inorganic filler and an elastomer. The silanes include those containing an aromatic group having an unsaturated substituent, such as triethoxy(4-vinylphenethyl)silane and 3-(N-styrylmethyl-2-aminoethylamino)propyltriethoxysilane, and those containing a heterocyclic ring such as N-(3-triethoxysilylpropyl)-dihydroimidazole and 1-(3-triethoxysilylpropyl)-pyrrole.

Other examples of hydrolysable silanes which have been proposed as coupling agents include unsaturated silanes containing an ester group, such as an acryloxypropyltrialkoxysilane, described in WO-A-2010/125124.

The paper 'Molecular recognition by a silica-bound fullerene derivative' by A. Bianco et al in J. Am. Chem. Soc 1997, volume 119, at pages 7550-7554 describes N-[3-(triethoxysily)propyl]-2-carbomethoxyaziridine and its reaction with fullerene.

EP1942161 describes N-(3-diethoxymethylsilyl)propyl 2-carboethoxy aziridine. The European Journal of Organic Chemistry, Vol. 13, 2006, pages 2934-2941 describes the synthesis of methyl N-(3-(Trialkoxysilyl)-propyl)aziridine-2-carboxylates. The Journal of the American Chemical Society, Vol. 119(32), 1997, pages 7550-7554 and Tetrahedron, Vol. 57(32), 2001, pages 6997-7002 describe MeO2C-(Az)-(CH2)3Si(Oet)3.

A hydrolysable silane according to the present invention has the formula Y—OC(O)-(Az)-Z wherein Y and Z each represent a hydrocarbyl or substituted hydrocarbyl group having 1 to 40 carbon atoms, at least one of Y and Z being a group of the formula $R_aR'_{3-a}Si$-A in which R represents a hydrolysable group; R' represents a hydrocarbyl group having 1 to 8 carbon atoms; a has a value in the range 1 to 3 inclusive; and A represents a divalent organic spacer linkage having at least one carbon atom, provided that when Z is a 3-(triethoxysilyl)propyl group Y has at least 2 carbon atoms. Z is on the nitrogen atom of the (Az) ring.

The hydrolysable silanes of the invention are capable of bonding strongly to diene elastomers under the processing conditions used for producing elastomer products such as tyres, reacting through the aziridine ring which reacts with C=C bonds of the elastomer through cycloaddition. The hydrolysable silanes of the invention are also capable of bonding strongly to fillers through hydrolysis of the silane group, thus forming very effective coupling agents.

The hydrolysable silanes of the invention can in general be prepared by reacting an alkyl or substituted alkyl 2,3-dibromopropionate of the formula Y—OC(O)—CHBr—CH₂Br with an amine of the formula Z—NH₂.

The substituted alkyl 2,3-dibromopropionates of the formula Y—OC(O)—CHBr—CH₂Br in which Y is a group of the formula $R_aR'_{3-a}$Si-A-, that is the substituted alkyl 2,3-dibromopropionates of the formula $R_aR'_{3-a}$Si-A-OC(O)—CHBr—CH₂Br, where R, R', a and A are defined as above, are new compounds. They can be prepared by the reaction of an acrylate of the formula $R_aR'_{3-a}$Si-A-OC(O)—CH=CH₂ with bromine at ambient temperature or below. Other 2,3-dibromopropionates of the formula Y—OC(O)—CHBr—CH₂Br can similarly be prepared from an acrylate of the formula Y—OC(O)—CH=CH₂ with bromine.

In the hydrolysable silanes of the invention, at least one of Y and Z is a group of the formula $R_aR'_{3-a}$Si-A in which R represents a hydrolysable group. The hydrolysable group can for example be an alkoxy or acyloxy group. Hydrolysable groups in which each group R is an alkoxy group having 1 to 4 carbon atoms such as methoxy, ethoxy, propoxy, isopropoxy or butoxy may be preferred, although other alkoxy groups having up to 8 carbon atoms can be used. Since the alcohol corresponding to the alkoxy group is released on hydrolysis, the most preferred alkoxy group is usually ethoxy. An example of a suitable acyloxy group is acetoxy. Preferably both Y and Z contain a silane.

Hydrolysable silanes in which a=3 may be preferred as having the maximum number of hydrolysable groups. Examples of groups of the formula $R_aR'_{3-a}$Si-A in which a=3 include trialkoxysilylalkyl groups such as triethoxysilylalkyl or trimethoxysilylalkyl groups, or triacetoxysilylalkyl groups. However hydrolysable silanes in which a=2 or a=1 are also useful coupling agents. In such hydrolysable silanes the group R' is a hydrocarbyl group having 1 to 8 carbon atoms. Preferred groups R' include alkyl groups having 1 to 4 carbon atoms such as methyl or ethyl, but R' can be an alkyl group having more carbon atoms such as hexyl or 2-ethylhexyl or can be an aryl group such as phenyl. Examples of groups of the formula $R_aR'_{3-a}$Si-A in which a=2 include diethoxymethylsilylalkyl, diethoxyethylsilylalkyl, dimethoxymethylsilylalkyl or diacetoxymethylsilylalkyl groups.

In the group of the formula $R_aR'_{3-a}$Si-A, A represents an alkylene group having 2 to 6 carbon atoms. Preferred examples of groups A are —(CH₂)₃—, —(CH₂)₄—, and —CH₂CH(CH₃)CH₂— groups. The group of the formula $R_aR'_{3-a}$Si-A can for example be a 3-(triethoxysilyl)propyl, 4-(triethoxysilyl)butyl, 2-methyl-3-(triethoxysilyl)propyl, 3-(trimethoxysilyl)propyl, 3-triacetoxysilylpropyl, 3-(diethoxymethylsilyl)propyl, 3-(diethoxyethylsilyl)propyl, 3-(dimethoxymethylsilyl)propyl or 3-(diacetoxymethylsilyl) propyl group.

In the hydrolysable silanes in which Y is a group of the formula $R_aR'_{3-a}$Si-A-, Z can be any hydrocarbyl or substituted hydrocarbyl group having 1 to 40 carbon atoms. Z can for example be an alkyl group having 1 to 6 carbon atoms such as methyl, ethyl, butyl or hexyl, or can be a longer chain alkyl group, or can be an aryl group having 6 to 10 carbon atoms such as phenyl or tolyl or an aralkyl group such as benzyl or 2-phenylpropyl. Z can alternatively be a substituted hydrocarbyl group such as a hydroxyalkyl, aminoalkyl, or alkoxyalkyl group or a group of the formula

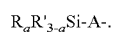

$R_aR'_{3-a}$Si-A-.

Similarly in the hydrolysable silanes in which Z is a group of the formula $R_aR'_{3-a}$Si-A—, Y can in general be any hydrocarbyl or substituted hydrocarbyl group having 1 to 40 carbon atoms, subject to the proviso that when Z is a 3-(triethoxysilyl)propyl group Y has at least 2 carbon atoms. Y can for example be an alkyl group having 1 to 10 or more carbon atoms, an aryl group having 6 to 10 carbon atoms, an aralkyl group or a substituted hydrocarbyl group.

Thus the hydrolysable silane may have the formula Y—OC(O)-(Az)-A'-Si-R*$_a$R"$_{3-a}$ wherein R* represents a hydrolysable group; R" represents a hydrocarbyl group having 1 to 8 carbon atoms; a has a value in the range 1 to 3 inclusive; A' represents a divalent organic spacer linkage having at least one carbon atom; and Y represents a hydrocarbyl or substituted hydrocarbyl group having 1 to 40 carbon atoms. For example the Z moiety may contain at least one group R* which is a methoxy group, or may contain at least one group R* which is an alkoxy group having 3 to 8 carbon atoms, or the -A'-Si-R*$_a$R"$_{3-a}$ moiety may contain at least one R" group. For any -A'-Si-R*$_a$R"$_{3-a}$ moiety, Y may represent an alkyl group having 2 to 10 or more carbon atoms, an aryl group having 6 to 10 carbon atoms, an aralkyl group or a substituted hydrocarbyl group.

Hydrolysable silanes in which both Y and Z are substituted hydrocarbyl groups of the formula R$_a$R'$_{3-a}$Si-A- are particularly preferred examples of hydrolysable silanes of the invention. Examples of such hydrolysable silanes include

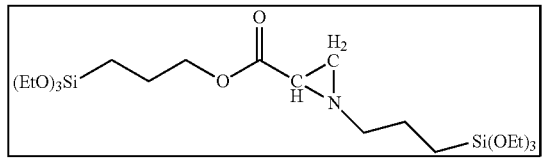

and similar silanes in which one or both of the 3-(triethoxysilyl)propyl groups is replaced by a different R$_a$R'$_{3-a}$Si-A- group selected from those listed above.

Other examples of hydrolysable silanes comprise silanes having a substituted C atom on the Az ring. For example it can be:

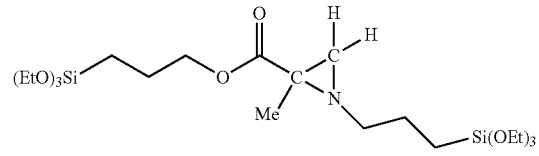
methacryloxysilane

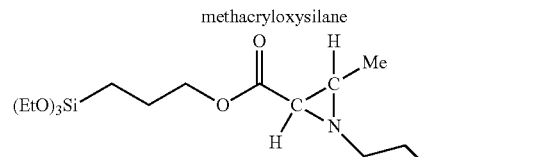
crotonoxysilane

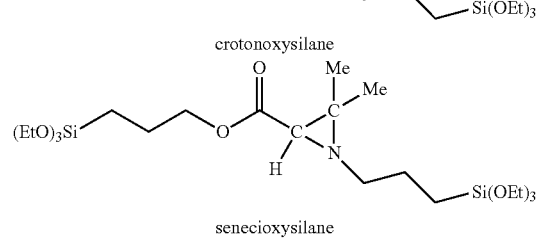
senecioxysilane

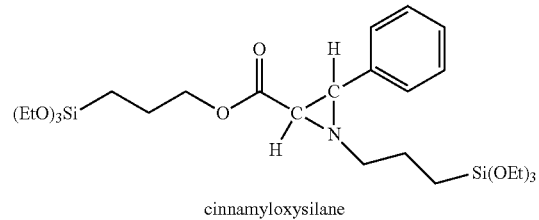
cinnamyloxysilane

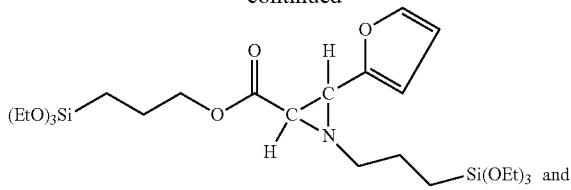
furanacryloxysilane

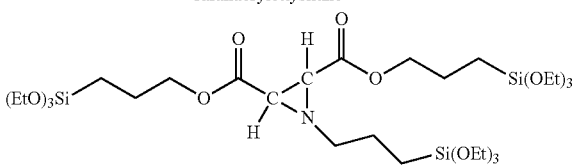 and

A hydrolysable silane of the formula Y—OC(O)-(Az)-Z wherein Y and Z each represent a hydrocarbyl or substituted hydrocarbyl group having 1 to 40 carbon atoms, at least one of Y and Z being a group of the formula R$_a$R'$_{3-a}$Si-A in which R represents a hydrolysable group; R' represents a hydrocarbyl group having 1 to 8 carbon atoms; a has a value in the range 1 to 3 inclusive; and A represents a divalent organic spacer linkage having at least one carbon atom, Az represents an aziridine ring wherein Z is bonded to Az through its nitrogen atom, provided that when in Z, A is a propyl group Y has at least 3 carbon atoms and provided that when Y is a silane, Z can either be a silane or alkyl, aryl or substituted hydrocarbyl group A hydrolysable silane according to claim 1 of the formula R$_a$R'$_{3-a}$Si-A-OC(O)-(Az)-Z wherein R, R', A and a are defined as in claim 1 and Z represents a hydrocarbyl or substituted hydrocarbyl group having 1 to 40 carbon atoms.

A hydrolysable silane according to claim 1 or claim 2, characterised in that each group R is an alkoxy group having 1 to 4 carbon atoms.

A hydrolysable silane according to claim 3, characterised in that each group R is an ethoxy group.

A hydrolysable silane according to any of claims 1 to 4, characterised in that a=3.

A hydrolysable silane according to any of claims 2 to 5, characterised in that A represents an alkylene group having 2 to 6 carbon atoms.

A hydrolysable silane according to any of claims 2 to 6, characterised in that Z represents an alkyl group having 1 to 6 carbon atoms.

A hydrolysable silane according to any of claims 2 to 6, characterised in that Z represents an aryl group having 6 to 10 carbon atoms.

A hydrolysable silane according to any of claims 2 to 6, characterised in that Z represents a substituted alkyl group of the formula -A'-SiRaR'3-a in which R, R' and a are defined as in claim 1 and A' represents a divalent organic spacer linkage having at least one carbon atom separating the silicon atom from the aziridine ring.

The hydrolysable silane of the formula (C$_2$H$_5$O)$_3$Si—(CH$_2$)$_3$—OC(O)-Az-(CH$_2$)$_3$—Si(C$_2$H$_5$O)$_3$.

A hydrolysable silane according to claim 1 of the formula Y—OC(O)-(Az)-A'-Si-R*$_a$R"$_{3-a}$ wherein R* represents a hydrolysable group; R" represents a hydrocarbyl group having 1 to 8 carbon atoms; a has a value in the range 1 to 3 inclusive; A' represents a divalent organic spacer linkage having at least one carbon atom; and Y represents a hydrocarbyl or substituted hydrocarbyl group having 1 to 40 carbon atoms.

A hydrolysable silane according to claim 11, characterised in that the Z moiety contains at least one group R* which is a methoxy group.

A hydrolysable silane according to claim 11, characterised in that the Z moiety contains at least one group R* which is an alkoxy group having 3 to 8 carbon atoms.

A hydrolysable silane according to any of claims 11 to 13, characterised in that the Z moiety contains at least one R" group.

A hydrolysable silane according to any of claims 11 to 14, characterised in that Y represents an alkyl group having 2 to 10 carbon atoms.

A process for the preparation of a hydrolysable silane of the formula Y—OC(O)-(Az)-Z as defined in claim 1, characterised in that an alkyl or substituted alkyl 2,3-dibromopropionate of the formula Y—OC(O)—CHBr—CH$_2$Br is reacted with an amine of the formula Z—NH$_2$ A substituted alkyl 2,3-dibromopropionate of the formula R$_a$R'$_{3-a}$Si-A-OC(O)—CHBr—CH$_2$Br, wherein R represents a hydrolysable group; R' represents a hydrocarbyl group having 1 to 8 carbon atoms; a has a value in the range 1 to 3 inclusive; and A represents a divalent organic spacer linkage having at least one carbon atom.

Examples for the preparation of hydrolysable silanes that are reactive towards diene elastomers.

EXAMPLE 1

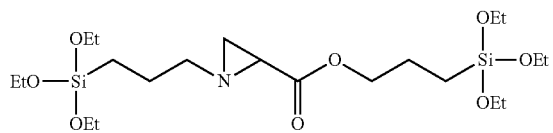 [SMILES: CCO[Si](CCCOC(=O)C1CN1CCC[Si](OCC)(OCC)OCC)(OCC)OCC]

Detailed synthesis of N-(3-triethoxysilylpropyl)aziridine-2-(3-triethoxysilylpropyl)carboxylate. A 500 ml two necked round bottom flask, fitted with a condenser, nitrogen sweep and magnetic stirrer, was charged with 23.4 g 3-aminopropyltriethoxysilane, 27.8 g triethylamine and 160 ml toluene and inerted with nitrogen. To this ice-cold mixture was added drop-wise a solution of 46.0 g (3-triethoxysilylpropyl)-2,3-dibromopropionate in 160 ml toluene. Mixture was refluxed for 6 hours and solids filtered off over diatomaceous earth. Solvent and volatiles were removed in vacuo affording the aziridine as a light orange liquid. Formation of the aziridine ring was confirmed by nuclear magnetic resonance spectroscopy.

EXAMPLE 2

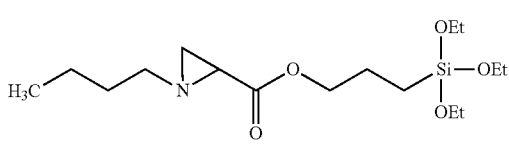 [SMILES: CCCCN1CC1C(=O)OCCC[Si](OCC)(OCC)OCC]

Detailed synthesis of N-(butyl) aziridine-2-(3-triethoxysilylpropyl) carboxylate. A 500 ml two necked round bottom flask, fitted with a condenser, nitrogen sweep and magnetic stirrer, was charged with g 7.7 g n-butylamine, 27.8 g triethylamine and 160 ml toluene and inerted with nitrogen. To this ice-cold mixture was added drop-wise a solution of 46.0 g (3-triethoxysilylpropyl)-2,3-dibromopropionate in 160 ml toluene. Mixture was refluxed for 6 hours and solids filtered off over diatomaceous earth. Solvent and volatiles were removed in vacuo affording the aziridine as a light orange liquid. Formation of the aziridine ring was confirmed by nuclear magnetic resonance spectroscopy.

EXAMPLE 3

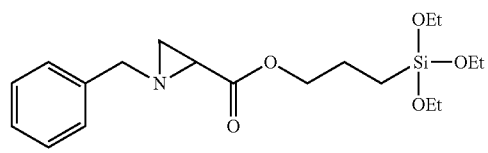 [SMILES: CCO[Si](CCCOC(=O)C1CN1Cc1ccccc1)(OCC)OCC]

Detailed description of the N-benzyl azaridine 2-(3-triethoxysilylpropyl)carboxylate. A 1 L two-necked round bottom flask, fitted with a condenser, nitrogen sweep and magnetic stirrer, was charged with 14.1 g benzylamine, 33.2 g triethylamine and 160 ml toluene and inerted with nitrogen. To this ice-cold mixture was added drop-wise a solution of 57.2 g (3-triethoxysilylpropyl)-2,3-dibromopropionate in 160 ml toluene. Mixture was refluxed for 6 hours and solids filtered off over diatomaceous earth. Solvent and volatiles was removed in vacuo affording the aziridine as a light orange liquid. Formation of the aziridine ring was confirmed by nuclear magnetic resonance spectroscopy.

PROPHETIC EXAMPLE 1

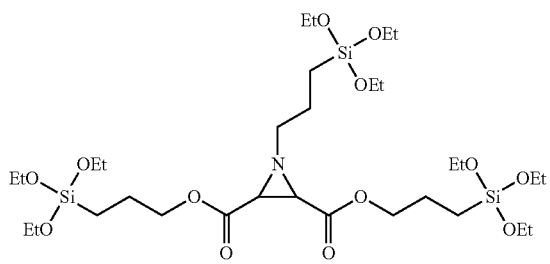 [SMILES: CCO[Si](CCCOC(=O)C1C(C(=O)OCCC[Si](OCC)(OCC)OCC)N1CCC[Si](OCC)(OCC)OCC)(OCC)OCC]

Detailed synthesis of N-(3-triethoxysilylpropyl)aziridine-2,3-bis(3-triethoxysilylpropylcarboxylate). A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 72.2 g bis(3-triethoxysilylpropyl)-2,3-dibromosuccinate in 160 ml toluene. Mixture will be refluxed for 6 hours and solids filtered off over diatomaceous earth. Solvent and volatiles will be removed in vacuo affording the aziridine as a light orange liquid. Formation of the aziridine ring will be confirmed by nuclear magnetic resonance spectroscopy.

PROPHETIC EXAMPLE 2

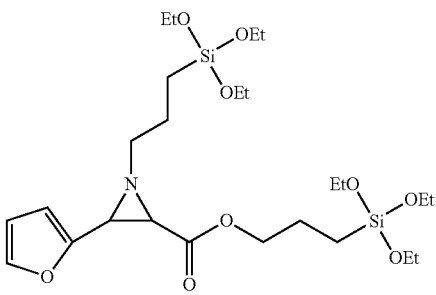 [SMILES: CCO[Si](CCCOC(=O)C1C(c2ccco2)N1CCC[Si](OCC)(OCC)OCC)(OCC)OCC]

Detailed synthesis of N-(3-triethoxysilylpropyl)aziridine-2-(2-furyl)-3-(3-triethoxysilylpropylcarboxylate). A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 53.1 g 2,3-dibromo-3-(2-furyl)propionic acid (3-triethoxysilylpropyl)ester in 160 ml toluene. Mixture will be refluxed for 6 hours and solids filtered off over diatomaceous earth. Solvent and volatiles will be removed in vacuo affording the aziridine. Formation of the aziridine ring will be confirmed by nuclear magnetic resonance spectroscopy.

PROPHETIC EXAMPLE 3

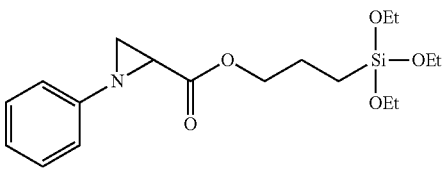 [SMILES: CCO[Si](CCCOC(=O)C1CN1c1ccccc1)(OCC)OCC]

Detailed description of the N-phenyl-2-(3-triethoxysilylpropylcarboxylate)aziridine. A 1 L two-necked round bottom flask, fitted with a condenser, nitrogen sweep and magnetic stirrer, will be charged with 12.7 g aniline, 34.5 g triethylamine and 160 ml toluene and inerted with nitrogen. To this ice-cold mixture will be added drop-wise a solution of 59.4 g (3-triethoxysilylpropyl)-2,3-dibromopropionate in 160 ml toluene. Mixture will be refluxed for 6 hours and solids filtered off over diatomaceous earth. Solvent and volatiles will be removed in vacuo affording the aziridine. Formation of the aziridine ring will be proven by nuclear magnetic resonance spectroscopy.

PROPHETIC EXAMPLE 4

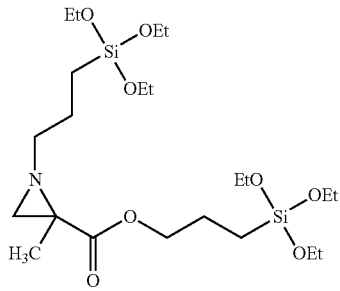 [SMILES: CCO[Si](CCCOC(=O)C1(C)CN1CCC[Si](OCC)(OCC)OCC)(OCC)OCC]

Detailed synthesis of N-(3-triethoxysilylpropyl)-2-methyl-2-(3-triethoxysilylpropylcarboxylate)aziridine. A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 47.6 g 2,3-dibromo-2-methylpropionic acid (3-triethoxysilylpropyl)ester in 160 ml toluene. Mixture will be refluxed for 6 hours and solids filtered off over diatomaceous earth. Solvent and volatiles will be removed in vacuo affording the aziridine. Formation of the aziridine ring will be confirmed by nuclear magnetic resonance spectroscopy.

PROPHETIC EXAMPLE 5

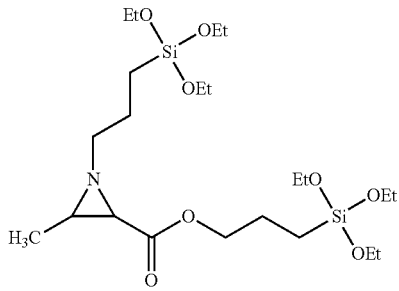 [SMILES: CCO[Si](CCCOC(=O)C1C(C)N1CCC[Si](OCC)(OCC)OCC)(OCC)OCC]

Detailed synthesis of N-(3-triethoxysilylpropyl)-2-methyl-3-(3-triethoxysilylpropylcarboxylate)aziridine. A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 47.6 g 2,3-dibromobutyric acid (3-triethoxysilylpropyl)ester in 160 ml toluene. Mixture will be refluxed for 6 hours and solids filtered off over diatomaceous earth. Solvent and volatiles will be removed in vacuo affording the aziridine. Formation of the aziridine ring will be confirmed by nuclear magnetic resonance spectroscopy.

PROPHETIC EXAMPLE 6

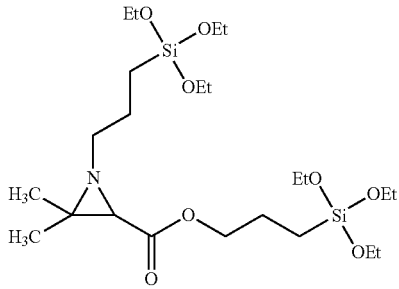 [SMILES: CCO[Si](CCCOC(=O)C1N(CCC[Si](OCC)(OCC)OCC)C1(C)C)(OCC)OCC]

Detailed synthesis of N-(3-triethoxysilylpropyl)-2,2-dimethyl-3-(3-triethoxysilylpropylcarboxylate)aziridine. A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 49.1 g 2,3-dibromo-3-methylbutyric acid (3-triethoxysilylpropyl)ester in 160 ml toluene. Mixture will be refluxed for 6 hours and solids filtered off over diatomaceous earth. Solvent and volatiles will be removed in vacuo affording the aziridine. Formation of the aziridine ring will be confirmed by nuclear magnetic resonance spectroscopy.

PROPHETIC EXAMPLE 7

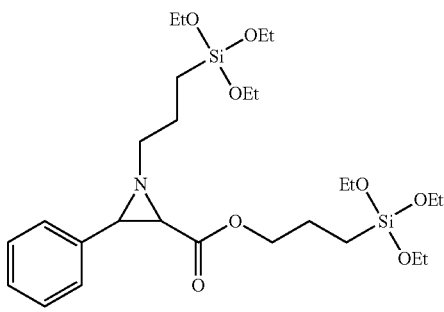 [SMILES: CCO[Si](CCCOC(=O)C1C(c2ccccc2)N1CCC[Si](OCC)(OCC)OCC)(OCC)OCC]

Detailed synthesis of N-(3-triethoxysilylpropyl)-2-phenyl-3-(3-triethoxysilylpropylcarboxylate)aziridine. A 500 ml two necked round bottom flask, fitted with a condenser, nitrogen sweep and magnetic stirrer, will be charged with 23.4 g 3-aminopropyltriethoxysilane, 27.8 g triethylamine and 160 ml toluene and inerted with nitrogen. To this ice-cold mixture will be added drop-wise a solution of 54.2 g 2,3-dibromo-3-phenylpropionic acid (3-triethoxysilylpropyl)ester in 160 ml toluene. Mixture will be refluxed for 6 hours and solids filtered off over diatomaceous earth. Solvent and volatiles will be removed in vacuo affording the aziridine. Formation of the aziridine ring will be confirmed by nuclear magnetic resonance spectroscopy.

The invention claimed is:

1. A hydrolysable silane of the formula $R_aR'_{3-a}Si$-A-OC(O)-(Az)-Z wherein Z represents a hydrocarbyl or substituted hydrocarbyl group having 1 to 40 carbon atoms; R represents a hydrolysable group; R' represents a hydrocarbyl group having 1 to 8 carbon atoms; a has a value in the range 1 to 3 inclusive; and A represents a divalent organic spacer linkage having at least one carbon atom, Az represents an aziridine ring wherein Z is bonded to Az through its nitrogen atom.

2. A hydrolysable silane according to claim 1, characterised in that each group R is an alkoxy group having 1 to 4 carbon atoms.

3. A hydrolysable silane according to claim 2, characterised in that each group R is an ethoxy group.

4. A hydrolysable silane according to claim 1, characterised in that a=3.

5. A hydrolysable silane according to claim 1, characterised in that A represents an alkylene group having 2 to 6 carbon atoms.

6. A hydrolysable silane according to claim 1, characterised in that Z represents an alkyl group having 1 to 6 carbon atoms.

7. A hydrolysable silane according to claim 1, characterised in that Z represents an aryl group having 6 to 10 carbon atoms.

8. A hydrolysable silane according to claim 1, characterised in that Z represents a substituted alkyl group of the formula -A'-$SiR_aR'_{3-a}$ in which R, R' and a are defined as in claim 1 and A' represents a divalent organic spacer linkage having at least one carbon atom separating the silicon atom from the aziridine ring.

9. A hydrolysable silane according to claim 1 of the formula $(C_2H_5O)_3Si$—$(CH_2)_3$—OC(O)-Az-$(CH_2)_3$—Si$(C_2H_5O)_3$.

10. A process for the preparation of a hydrolysable silane of the formula $R_aR'_{3-a}Si$-A-OC(O)-(Az)-Z as defined in claim 1, characterised in that a substituted alkyl 2,3-dibromopropionate of the formula $R_aR'_{3-a}Si$-A-OC(O)—CHBr—$CH_2Br$ is reacted with an amine of the formula Z—$NH_2$.

11. A substituted alkyl 2,3-dibromopropionate of the formula $R_aR'_{3-a}Si$-A-OC(O)—CHBr—$CH_2Br$, wherein R represents a hydrolysable group; R' represents a hydrocarbyl group having 1 to 8 carbon atoms; a has a value in the range 1 to 3 inclusive; and A represents a divalent organic spacer linkage having at least one carbon atom.

* * * * *